US006365182B1

(12) United States Patent
Khankari et al.

(10) Patent No.: US 6,365,182 B1
(45) Date of Patent: *Apr. 2, 2002

(54) ORGANOLEPTICALLY PLEASANT IN-MOUTH RAPIDLY DISINTEGRABLE POTASSIUM CHLORIDE TABLET

(75) Inventors: Rajendra K. Khankari, Maple Grove; John Hontz, Plymouth; Sara J. Chastain, Maple Grove, all of MN (US)

(73) Assignee: Cima Labs Inc., Eden Prairie, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/132,837

(22) Filed: Aug. 12, 1998

(51) Int. Cl.$^7$ .............................. A61K 9/46; A61K 9/22; A61K 9/16; A61K 9/50
(52) U.S. Cl. ....................... 424/466; 424/468; 424/494; 424/497
(58) Field of Search ................................. 424/466, 468, 424/474, 494, 497, 495

(56) References Cited

U.S. PATENT DOCUMENTS

| | | |
|---|---|---|
| 3,962,417 A | 6/1976 | Howell |
| 4,613,497 A | 9/1986 | Chavkin |
| 4,639,368 A | 1/1987 | Niazi et al. |
| 4,687,662 A | 8/1987 | Schobel |
| 4,753,792 A | 6/1988 | Aberg |
| 4,863,743 A * | 9/1989 | Hsiao et al. ................. 424/476 |
| 4,940,588 A | 7/1990 | Sparks et al. |
| 5,055,306 A | 10/1991 | Barry et al. |
| 5,178,878 A * | 1/1993 | Wehling et al. ............. 424/466 |
| 5,225,197 A | 7/1993 | Bolt et al. |
| 5,464,632 A | 11/1995 | Cousin et al. |
| 5,607,697 A * | 3/1997 | Alkire et al. ................ 424/495 |
| 5,651,984 A * | 7/1997 | Powell ........................ 424/465 |

FOREIGN PATENT DOCUMENTS

GB      3160      10/1872

OTHER PUBLICATIONS

U.S. Pharmacopoeia No. 23, 1995, Chap. 1216, "Tablet Friability".
Physicians' Desk Reference, 1999 Edition, K–DUR® p. 1454–1456.

* cited by examiner

*Primary Examiner*—Diana Dudash
*Assistant Examiner*—Alysia Berman
(74) *Attorney, Agent, or Firm*—Lerner, David, Littenberg, Krumholz & Mentlik, LLP

(57) ABSTRACT

The present invention relates to a potassium containing dosage form which is capable of rapidly disintegrating in a patient's mouth to form an easy to swallow slurry.

24 Claims, No Drawings

ORGANOLEPTICALLY PLEASANT IN-MOUTH RAPIDLY DISINTEGRABLE POTASSIUM CHLORIDE TABLET

FIELD OF THE INVENTION

The invention relates to the fields of pharmacy and medicine and in particular to dosage forms for the delivery of potassium.

BACKGROUND OF THE INVENTION

Potassium supplementation is used for patients who have hypokalemia without metabolic alkalosis, in digitalis intoxication and in patients with hypokalemic familial periodic paralysis. It is also used for the prevention of hypokalemia in patients at risk therefor. Potassium is a naturally occurring ion required for normal cell function. The $K^+$ ion can be depleted during therapies with diuretics, frequently used in treating hypertension and congestive heart failure. Oncology patients on highly restrictive diets also frequently need potassium replacement.

The typical potassium replacement patient is over 65 years old. Frequently, the patient is significantly older. Patients in this demographic may have difficulty swallowing large tablets for many reasons including dysphagia, a changed or diminished "gag" reflex. Oncology patients also are prone to swallowing difficulties. This would make swallowing tablets difficult under the best of circumstances. However, the current potassium replacement does not offer the best of circumstances. The tablets tend to be large, chalky, desiccating and difficult to swallow.

One of the leading potassium supplements is a potassium chloride formulation sold under the trademark K-DUR® available from Key Pharmaceuticals, Inc., Galloping Hill Road, Kenilworth, N.J. 07033. The approved label for K-DUR® tablets indicates that each tablet should be taken with a meal and with a full glass of water. Each dose should be taken without crushing, chewing or sucking the tablet. Patients who have difficulty in swallowing whole tablets may break the tablet in half and attempt to take each half separately with a glass of water. For those who still can't swallow the tablet, the label instructs one in how to prepare an aqueous water suspension. However, dispersing K-DUR® in water is inconvenient, can be difficult for older individuals and may require an excess of water to retrieve the entire dose from a glass. This poses a potential threat to patients with significant fluid restriction and an inconvenience to patients with incontinence problems.

The only alternative to the current potassium supplement is potassium given in a liquid form. However, these liquids have an extremely unpleasant metallic taste. The result is patients who are non-compliant. Non-compliance with potassium replacement therapy has been shown to lead to clinically significant health risks such as cardiac arrhythmia and sudden death. Therefore, there is a significant need for finding effective alternative delivery systems for potassium replacement therapy.

SUMMARY OF THE INVENTION

The present invention solves this need by providing an orally disintegrable tablet suitable for use in the delivery of potassium. The tablet contains between about 50 and about 80% coated potassium chloride crystals by weight of the tablet. These coated potassium chloride crystals have a particle size ranging from between about 100 to about 2,000 microns and include between about 10 and about 20% of a coating based on the weight of the coated potassium chloride crystals. The coating is generally an extended release coating. The tablet also includes between about 5 and about 35% of a rapidly dissolvable sugar or sugar alcohol filler. The rapidly dissolvable sugar or sugar alcohol filler has a particle size selected to be complementary to the particle size of the coated potassium chloride crystals and generally ranges between about 300 and about 1,500 microns. The tablet also includes between about 0 and about 15% of a binder, including insoluble filler-binders, between about 1 and about 10% of a disintegrant; and between about 0 and about 15% of an effervescent couple. The sugar or sugar alcohol, binder disintegrant and effervescent couple are all provided in amounts based on the weight of the finished tablet.

In a particularly preferred embodiment, the tablet of the present invention weighs between about 1200 and about 3000 mg and contains between about 5 and about 25 milliequivalents (mEq) of potassium. More preferable, the tablet will weigh between about 1300 and about 2800 mg and contain between about 10 and about 20 mEq of potassium.

The present invention solves the aforementioned problems by using some rather counterintuitive insights. First, the instructions approved by the Food and Drug Administration for use of potassium chloride tablets specifically direct one not to crush, chew or suck on such supplements. However, by employing just such a suckable formulation, it has been unexpectedly found that one is able to obtain an organoleptically pleasing dosage form—one that can enhance compliance. Second, one of the more daunting aspects of current potassium supplements is their relative size, chalkiness and desiccating nature. Particularly for older patients, such tablets present a significant problem. To overcome the problem of a large chalky tablet, one would seek to use either an entirely different dosage form (liquid, etc.), or find a way of reducing the tablet's size and volume. However, it has now been found that by actually increasing the amount of material administered, and to some lesser extent, the size of the resulting tablet, one is nonetheless able to obtain a dosage form which overcomes the difficulties and inabilities of the patients most likely to use same. It is indeed ironic that while one would think of making the potassium containing tablet lighter and/or smaller to overcome compliance issues, the answer was actually found by going in the completely opposite direction.

Third and even more surprisingly, if one were to ignore the instructions of the manufacturer, take a commercially available potassium chloride supplement tablet, and allow it to dissolve in their mouth, two things would happen. First, the tablet which contains upwards of 90% or more coated potassium chloride would take between about 40 seconds and a minute to actually disintegrate. Second, because the tablet contains such a significant quantity of insoluble coated active material, the results of disintegration would the formation of a "sandbox" in the patient's mouth; a most unpleasant sensation to say the least. This would be both unpleasant in the mouth and difficult to swallow.

It has now been found that by decreasing the relative proportion of active ingredients and supplementing with a rapidly water dissolvable filler, by selecting fillers and materials having relatively similar particle size to the coated active, one is actually able to obtain a tablet which is rapidly disintegrable in the mouth without the objectionable organoleptic properties of present formulations. Moreover, despite the fact that the size and volume of the tablet have actually been increased, the disintegration time is maintained and preferably decreased. A commercially available 10 milliequivalent potassium chloride tablet can dissolve in the mouth between 30 seconds and a minute as previously stated. In truth, disintegration times of about 45 seconds or more are to be expected. An otherwise equivalent formulation of the present invention, despite being 50% greater in overall weight nonetheless can substantially disintegrate in under 30 seconds.

The use of organoleptically pleasing ingredients such as a mild level of effervescence to stimulate the production of saliva and accentuate disintegration, and rapidly dissolving filler such as mannitol (mannitol has a negative heat of solution which further adds to the organoleptically pleasing nature of the formation), one obtains a dosage form which rapidly disintegrates and forms a watery slurry which is much more organoleptically pleasing and very easy to swallow.

DETAILED DESCRIPTION OF THE PREFERRED EMBODIMENT

In accordance with the present invention, "orally disintegrable" means that the tablet will disintegrate substantially into its component parts (e.g. the insoluble coated particles, insoluble disintegrant, etc.) within 45 seconds or less and more preferably within about 30 seconds or less. For very large tablets, i.e., 2,000 mg or above, greater than 30 seconds may be required. Therefore, it is to be understood that when disintegration times of 30 seconds or less may be described, that means that the tablet is substantially disintegrated in that time. When larger tablets are contemplated, while disintegration may not be complete in 30 seconds, roughly an amount of the tablet equivalent to that of a smaller tablet (<2,000 mg) will have disintegrated in that time period. "Dissolvable" or "dissolution," in accordance with the present invention, refers to certain components of the tablet of the present invention which are substantially soluble in water and saliva. At least about 50% by weight of such ingredients will dissolve and preferably within about 15 seconds of a tablet being placed in a patient's mouth.

Potassium chloride crystals in accordance with the present invention relates to a crystalline form of potassium chloride. Preferably, the tablet in accordance with the present invention contains between about 50 and about 80% of coated crystals of potassium chloride. This means that between 50 and 80% of the weight of the finished tablet is made up of such coated particles. More preferably, the amount of coated potassium chloride crystals ranges from between about 60–65% by weight and most preferably about 63% by weight.

The amount of potassium chloride provided must also be sufficient to be therapeutically useful. Therefore, the amount of potassium delivered should range from between about 5 and about 25 milliequivalents and preferably between about 10 and about 20 milliequivalents.

These coated particles should have a particle size ranging from between about 100 to about 2,000 microns, and more preferably between about 300 to about 1,500 microns.

Of these coated particles, between about 10 to about 20% by weight of the coated particles themselves is made up of the coating. Preferably, the amount of coating, by weight of the particles of the coated potassium chloride, ranges from between about 13 to about 17% and more preferably from between about 14 to about 16%.

The coating in accordance with the present invention is preferably an extended release coating. By extended release it is understood that while the coated particles are rapidly dispersed, in a matter of less than about 30 seconds, into the mouth, the potassium chloride itself is released from the particles in a manner that alters its otherwise normal release profile. By the use of these coatings, the time necessary between doses of potassium chloride can be extended relative to the use of the same quantity of uncoated particles or crystals. Preferably the extended release coatings in accordance with the present invention will provide for a release of potassium chloride, with as uniform a rate as possible, over a period of time ranging from between about 4 to about 24 hours and more preferably from between about 6 to about 24 hours.

Preferred extended release coatings in accordance with the present invention include, for example, cellulose ethers, cellulose esters, polymethacrylates and copolymers, polyvinylacetate copolymers and polyvinyl pyrrolidone. Cellulose ethers include methyl cellulose, hydroxypropylmethyl cellulose, ethyl cellulose, hydroxypropyl cellulose and carboxymethylethyl cellulose. Cellulose esters include hydroxypropylmethyl cellulose phthalate, cellulose-acetate phthalate, and hydroxypropylmethyl cellulose acetate succinate. Poly-methacrylates include, methacrylic acid/methyl methacrylate copolymers, methacrylic acid-methyl acrylate copolymers and dimethyl amino-methyl methacrylate copolymers. Polyvinyl acetate copolymers include vinylacetate/vinylpyrrolidone copolymers polyvinylacetate phthalate and PVP.

The tablet in accordance with the present invention also includes between about 5 and about 35% of a rapidly dissolvable sugar or sugar alcohol filler. This amount is based on the weight of the finished tablet. More preferably, the amount of such filler will range from between about 10 to about 25% by weight based on the tablet and most preferably between about 12 to about 18% by weight.

Rapidly dissolvable sugar and sugar alcohol in accordance with the present invention include, for example, mannitol, lactose, sucrose, maltose, dextrose, sorbitol, xylitol, maltitol, lactitol, and maltodextrins. Mannitol and other similar compounds having a negative heat of solution are preferred because they provide a particularly pleasant sensation enhancing the organoleptic experience of taking the tablet of the present invention. When used at all, only rapidly water soluble filler materials should be used.

Where necessary, granulated materials are used such that the particle size of the filler is complementary to that of the particle size of the coated potassium chloride crystals. "Complementary" does not mean that the particle sizes need be exactly the same. However, the greater the degree of similarity, the greater the homogeneity of the material. The greater homogeneity, in turn, results in much greater uniformity of disintegration and dissolution. The particle size of the filler should therefore range from between about 100 to about 1,800 and more preferably between about 150 to about 1,500 microns.

For tableting purposes, a binder is preferred. The binder should be present in an amount of between about 0 to about 15% by weight based on the weight of the tablet. Preferably, the binder will be present in an amount which is greater than zero and indeed, in an amount of between about 3 to about 15% and even more preferably between about 8 and about 12%. Water soluble binders are preferred. But generally, such binders are water insoluble. Therefore, the effort should be made to minimize the content of such binders as the higher the overall content of insoluble materials such as the coated active, the lower the overall organoleptic quality of the formulation. Certain binders such as a number of insoluble filler-binders including microcrystalline cellulose sold under the trade name "AVICEL" have additional advantageous properties that, despite their insolubility, make them nonetheless more desirable than other similar binders. A number of AVICEL formulations such as, for example, type PH 113 available from FMC Corporation, Princeton, N.J. can act as a dry binder. However, when placed in an aqueous environment such as, in a patient's mouth, the binder can actually aid in the disintegration of the tablet. In addition, microcrystalline cellulose imparts an almost creamy mouth feel which helps offset the negative impact of its insolubility. The use of such binders therefore helps reduce the overall amount of disintegrant which needs be used. Other binders include alginic acid, sodium alginate, starch, modified starches and other water swellable binders. Note that certain binders, such as AVICEL, can also be used and classified as disintegrants as is known in the industry.

Disintegrants are also desirable. Disintegrants, such as crospovidone (polyvinyl pyrrolidone ("PVP")) are generally water insoluble. While they add to the rapid disintegration of the formulation, their inclusion can also add to the total content of insoluble ingredients making it more difficult to strike a balance between disintegration/dissolution speed and the resulting organoleptic sensation. Preferably, the amount of disintegrant will range from between about 1 to about 10% by weight based on the weight of the tablet and more preferably between about 3 to about 7%. About 5% or less by weight is most preferred. Other disintegrants useful include sodium starch glycolate, croscarmallose sodium, microcrystalline cellulose and starch.

An effervescent couple is also preferred for use in accordance with the present invention. Although it is provided in a relatively small amount, the effervescent couple provides a number of advantages in the overall context of the present formulation. First, it aids in the disintegration of the tablet making it easier for the dissolvable constituents to dissolve and rapidly create a slurry. The presence of effervescence can also help stimulate the generation of saliva again facilitating disintegration, dissolution and the formation of an in-mouth slurry. Finally, many find the sensation of a mild amount of effervescence to be pleasing and this helps facilitate compliance by enhancing the organoleptic properties of the tablet.

The term effervescent couple(s) includes compounds which evolve gas. The preferred effervescent couples evolve gas by means of chemical reactions which take place upon exposure of the effervescent couple to water and/or to saliva in the mouth. The bubble or gas generating reaction is most often the result of the reaction of a soluble acid source and alkali metal carbonate or carbonate source. The reaction of these two general classes of compounds produces carbon dioxide gas upon contact with water included in saliva.

Such water activated materials should be kept in a generally anhydrous state with little or no absorbed moisture or in a stable hydrated form since exposure to water will prematurely disintegrate the tablet. The acid sources or acid may generally include food acids, acid anhydrides and acid salts. Food acids include citric acid, tartaric acid, malic acid, fumaric acid, adipic acid and succinic acids, etc. Because these acids are directly ingested, their overall solubility in water is less important than it would be if the effervescent tablet formulations of the present invention were intended to be dissolved in a glass of water. Acid anhydrides and acid of the above described acids may also be used. Acid salts may include sodium, dihydrogen phosphate, disodium dihydrogen pyrophosphate, acid citrate salts and sodium acid sulfite.

Carbonate sources include dry solid carbonate and bicarbonate salts such as sodium bicarbonate, sodium carbonate, potassium bicarbonate and potassium carbonate, magnesium carbonate and sodium sesquicarbonate, sodium glycine carbonate, L-lysine carbonate, arginine carbonate and amorphous calcium carbonate.

The effervescent couple of the present invention is not always based upon a reaction which forms carbon dioxide. Reactants which evolve oxygen or other gases which are safe are also considered within the scope. Where the effervescent couple includes two mutually reactive components, such as an acid source and a carbonate source, it is preferred that both components react completely. Therefore, an equivalent ratio of components which provides for equal equivalents is preferred. For example, if the acid used is diprotic, then either twice the amount of a mono-reactive carbonate base, or an equal amount of a di-reactive base should be used for complete neutralization to be realized. However, in other embodiments of the present invention, the amount of either acid or carbonate source may exceed the amount of the other component. This may be useful to enhance taste and/or performance of a tablet containing an overage of either component. In this case, it is acceptable that the additional amount of either component may remain unreacted.

In general, the effervescent couple may be provided in an amount of between about 0 to about 15% by weight of the tablet. More preferably, it will be provided in an amount of 0 to about 5%. It is preferred, however, that the effervescent couple be provided in an amount which is greater than zero. Indeed, while neither a binder nor an effervescent couple is required to provide acceptable performance, the use of at least one of a binder end or effervescent couple is preferred. Most preferably, some amount of both are provided.

Remarkably, despite the relatively high percentage of insoluble ingredients, relatively little additional sweetener or flavor is needed. A formulation in accordance with the present invention weighing about 1400 milligrams, for example, may only require about 2.5 milligrams of aspartame at about 0.10 milligrams of natural and artificial flavors. To the extent that such sweeteners or flavors are necessary, they should e included in an amount generally below about 2%, preferably below about 1% and most preferably below about 0.5%. Other common excipients such as, tableting lubricants, colors and the like may also be included. Lubricants, such as magnesium stearate should also be included in an amount of less than about 2% by weight of the finished tablet, preferably less than about 1% and most preferably about 0.5% by weight. The same is true for other excipients.

Tablets according to the present invention can be manufactured by well-known tableting procedures. In common tableting processes, material which is to be tableted is deposited into a cavity, and one or more punch members are then advanced into the cavity and brought into intimate contact with the material to be pressed, whereupon compressive force is applied. The material is thus forced into conformity with the shape of the punches and the cavity. Hundreds, and even thousands, of tablets per minute can be produced in this fashion. Various tableting methods, well known to those skilled in the art, are comprehensively discussed throughout *Pharmaceutical Dosage Forms; Tablets*, Second Edition, edited by Herbert A. Lieberman et al., Copyright 1989 by Marcel Dekker, Inc., incorporated by reference herein, as well as other well known texts. Tablets should be compressed to a hardness of between about 10 and about 50 Newtons and preferably, about 15 to about 40 Newtons.

The tablets resulting from the present invention do not significantly alter the dissolution or release profile of the same quantity of coated potassium chloride crystals administered through conventional, commercially available formulations like K-DUR®. These physical properties can be measured by known USP procedures. Relative disintegration times are a bit more complicated to quantify. Equivalent tablets can be dropped into glasses of water and disintegration monitored and timed. But this is not really an accurate method as it does not fully simulate the process in vivo. The best way to assess in-mouth disintegration is by timing the disintegration of both tablets after being placed in a test subject's mouth. The mouth can be opened at various times to measure the progress.

EXAMPLE 1

The following ingredients were mixed to form a homogenous blend: potassium chloride containing 15% by weight of the extended release coating of ethyl cellulose and hydroxypropyl cellulose (882.4 milligrams per tablet), granular mannitol, USP (228.0 milligrams per tablet), microcrystalline cellulose, NF/Ph. Eur. (Avicel type Ph113) (140.0 milligrams per tablet), crospovidone NF (70.0 milligrams per tablet), sodium bicarbonate, No 1 USP (40.6 milligrams per tablet), citric acid, anhydrous fine granular, USP (29.4 milligrams per tablet), magnesium stearate, NF (7.0 milligrams per tablet), aspartame, NF (2.5 milligrams per tablet), mint flavor (0.10 milligrams per tablet) were blended. The blended material was then moved to a Korsch Model PH336 brand tablet press and compressed to a hardness of 22 Newtons in dies which produced ⅝ inch flat faced tablets with a beveled edge.

The resulting tablets had a tablet weight of approximately 1400 milligrams, while, at the same time, providing about 10 milliequivalents of potassium. A comparable tablet sold under the trademark K-DUR® providing the same amount of potassium weighs only approximately 950 milligrams. The tablets are of different shape with the K-DUR® tablet being oblong and the tablets of the present invention being a traditional round flat faced tablet. However, despite an increase in weight of greater than 50%, the overall size of the tablet did not increase a comparable amount. Moreover, the hardness of conventional K-DUR® tablets is significantly greater than that of the tablets in accordance with this example. Again, this is counterintuitive. One would expect that in order to obtain a more comparable size, despite the increase in weight of materials used, an equal or greater hardness would be necessary. The tablets of this example disintegrated in the mouth substantially completely within 30 seconds and resulted in a pleasant tasting, in-mouth slurry which was easy to swallow.

EXAMPLE 2

The following ingredients were mixed to form a homogeneous blend: potassium chloride (85% active) (63.03 weight percent per tablet);

granular mannitol, USP (16.29 weight percent per tablet); sodium bicarbonate, No. 1 USP (2.90 weight percent per tablet); citric acid, anhydrous, fine granular USP (2.10% weight percent per tablet); aspartame, NF (0.18 weight percent per tablet); magnesium stearate, NF (0.50% weight percent per tablet); microcrystalline cellulose (AVICEL PH113) (10.0 weight percent per tablet); crospovidone, (NF 5.00% weight percent per tablet) natural and artificial flavoring (0.01 weight percent per tablet). The blended ingredients were then transferred to a tablet press and compressed to a hardness of 22 Newtons in dies which produced ¹¹⁄₁₆" tablets as described in Example 1.

The resulting tablets had a tablet weight of approximately 2,800 mg, while, at the same time, providing about milliequivalents of potassium. As previously discussed, the resulting tablets in accordance with the present invention provided an excellent mouth feel and disintegrated within the mouth completely within about 30–40 seconds. Note: because of the large volume of material, complete disintegration took a bit longer.

EXAMPLE 3

Ten milliequivalent potassium chloride containing tablets were prepared as described in Example 1 having the following formulations: potassium chloride (85% active) (63.03 weight percent per tablet); granular mannitol (19.94 weight percent per tablet); sodium bicarbonate, No. 1 USP, (0.58 weight percent per tablet); citric acid anhydrous, fine granular USP (0.42 weight percent per tablet); magnesium stearate NF (1.0 weight percent per tablet); flavoring, (0.03 weight percent per tablet); microcrystalline cellulose (AVICEL PH200) (5.00 weight percent per tablet) and crospovidone, NF (10.00 weight percent per tablet). The materials were tableted to a hardness of 22 Newtons as previously described and disintegrated in the mouth within 30 seconds. The tablets had excellent mouth feel and the resulting slurry was easily swallowed.

EXAMPLE 4

Tablets were prepared as described in Example 3 having the following ingredients:

| Ingredient | % w/w per tablet |
| --- | --- |
| Potassium Chloride (85% active) | 63.03 |
| Granular Mannitol | 23.44 |
| Sodium Bicarbonate, No. 1 USP | 0.58 |
| Citric Acid Anhydrous, Fine Granular USP | 0.42 |
| Magnesium Stearate, NF | 1.00 |
| Mint Flavor IFF (SN027513) | 0.03 |
| Microcrystalline Cellulose - PH200 | 5.00 |
| Crospovidone, NF | 6.50 |
| TOTAL | 100.00 |

The materials were tableted to a hardness of 22 Newtons as previously described and disintegrated in the mouth within 30 seconds. The tablets had excellent mouth feel and the resulting slurry was easily swallowed.

EXAMPLE 5

Tablets were prepared as described in Example 3 having the following ingredients:

| Ingredient | % w/w per tablet |
| --- | --- |
| Potassium Chloride (85% active) | 63.03 |
| Granular Mannitol | 24.94 |
| Sodium Bicarbonate, No. 1 USP | 0.58 |
| Citric Acid Anhydrous, Fine Granular USP | 0.42 |
| Magnesium Stearate, NF | 1.00 |
| Mint Flavor IFF (SN027513) | 0.03 |
| Microcrystalline Cellulose - PH200 | 0.00 |
| Crospovidone, NF | 10.00 |
| TOTAL | 100.00 |

The materials were tableted to a hardness of 22 Newtons as previously described and disintegrated in the mouth within 30 seconds. The tablets had excellent mouth feel and the resulting slurry was easily swallowed.

EXAMPLE 6

Tablets were prepared as described in Example 3 having the following ingredients:

| Ingredient | % w/w per tablet |
| --- | --- |
| Potassium Chloride (85% active) | 63.03 |
| Granular Mannitol | 14.97 |
| Sodium Bicarbonate, No. 1 USP | 0.58 |
| Citric Acid Anhydrous, Fine Granular USP | 0.42 |
| Magnesium Stearate, NF | 1.00 |
| Microcrystalline Cellulose - PH200 | 10.00 |
| Crospovidone, NF | 10.00 |
| TOTAL | 100.00 |

The materials were tableted to a hardness of 22 Newtons as previously described and disintegrated in the mouth within 30 seconds. The tablets had excellent mouth feel and the resulting slurry was easily swallowed.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. An orally disintegrable tablet suitable for use in the delivery of potassium comprising: between about 50 and about 80% coated potassium chloride crystals by weight of the tablet, said coated potassium crystals having a particle size ranging from between about 100 to about 2,000 microns and including between about 10 and about 20% of an extended release coating based on the weight of the coated potassium chloride crystals; between about 10 and about 35% of a rapidly dissolvable sugar or sugar alcohol filler by weight of the tablet, said rapidly dissolvable sugar or sugar alcohol filler having a particle size selected to be complementary to the particle size of said coated potassium chloride crystals and being between about 150 and about 1,500 microns; between about 0 and about 15% of a binder by weight of the tablet; between about 3 and about 10% of a disintegrant by weight based on the weight of the tablet; and optionally between about 0 and about 15% of an effervescent couple based on the weight of the tablet wherein the tablet contains between about 5 and about 25 millieguivalents of potassium.

2. The orally disintegrable tablet of claim 1, wherein said coated potassium chloride crystals are provided in an amount of between 60 and about 65% by weight of the tablet.

3. The orally disintegrable tablet of claim 2, wherein said coated potassium chloride crystals are provided in an amount of about 63% by weight of the tablet.

4. The orally disintegrable tablet of claim 1, wherein said coated potassium chloride crystals have a particle size ranging from between about 300 to about 1,500 microns.

5. The orally disintegrable tablet of claim 1, wherein said coated potassium chloride crystals include between about 13 and about 17% of an extended release coating based on the weight of the coated potassium chloride crystals.

6. The orally disintegrable tablet of claim 5, wherein said coated potassium chloride crystals include between about 14 and about 16% of an extended release coating based on the weight of the coated potassium chloride crystals.

7. The orally disintegrable tablet of claim 1, wherein said extended release coating is selected from the group consisting of: cellulose ethers, cellulose esters, polymethacrylates and copolymers, polyvinylacetate copolymers and polyvinyl pyrrolidone.

8. The orally disintegrable tablet of claim 1, wherein said rapidly dissolvable sugar or sugar alcohol filler is provided in an amount of between about 10 and about 25% by weight of the tablet.

9. The orally disintegrable tablet of claim 8, wherein said rapidly dissolvable sugar or sugar alcohol filler is provided in an amount of between about 12 and about 18% by weight of the tablet.

10. The orally disintegrable tablet of claim 1, wherein said rapidly dissolvable sugar or sugar alcohol filler is selected from the group consisting of mannitol, lactose, sucrose, maltose, dextrose, sorbitol, xylitol, maltitol, lactitol and maltodextrins.

11. The orally disintegrable tablet of claim 10, wherein said rapidly dissolvable sugar or sugar alcohol filler is mannitol.

12. The orally disintegrable tablet of claim 1, wherein said binder is provided in an amount of between about 3 and about 15% by weight of the tablet.

13. The orally disintegrable tablet of claim 1, wherein said binder is selected from the group consisting of microcrystalline cellulose, alginic acid, sodium alginate and starch.

14. The orally disintegrable tablet of claim 1, wherein said disintegrant is provided in an amount of between about 3 and about 7% by weight of the tablet.

15. The orally disintegrable tablet of claim 14, wherein said disintegrant is provided in an amount of about 5% or less by weight of the tablet.

16. The orally disintegrable tablet of claim 1, wherein said disintegrant is selected from the group consisting of PVP, sodium starch glycolate, croscarmellose sodium, microcrystalline cellulose and starch.

17. The orally disintegrable tablet of claim 1, wherein said effervescent couple is provided in an amount of between about 0 and about 5% by weight of the tablet.

18. The orally disintegrable tablet of claim 1 wherein the amount of coated potassium chloride crystals is sufficient to provide between about 10 to about 20 milliequivalents of potassium.

19. An orally disintegrable tablet suitable for use in the delivery of potassium comprising: between about 60 and about 65% coated potassium chloride crystals by weight of the tablet, said coated potassium crystals having a particle size ranging from between about 300 to about 1,500 microns and including between about 13 and about 17% of an extended release coating based on the weight of the coated potassium chloride crystals; between about 10 and about 25% of a rapidly dissolvable sugar or sugar alcohol filler by weight of the tablet, said rapidly dissolvable sugar or sugar alcohol filler having a particle size selected to crystals and being between about 150 and about 1,500 microns; between about 0 and about 15% of a water insoluble binder by weight of the tablet; between about 3 and about 7% of a water insoluble disintegrant by weight based on the weight of the tablet; and between about 0 and about 5% of an effervescent couple based on the weight of the tablet, said tablet having a total weight of between about 1200 and about 3000 mg providing between about 10 and about 20 milliequivalents of potassium, having a hardness of between about 10 and about 50 Newtons and being capable of substantially disintegrating in the mouth within about 30 seconds.

20. The orally disintegrable tablet of claim 19 wherein said water insoluble binder is provided in an amount which is between greater than zero and about 15% by weight.

21. The orally disintegrable tablet of claim 19 wherein said effervescent couple is provided in an amount of between greater than zero and about 5% by weight.

22. A method of administering potassium chloride to patients in need of such treatment comprising the steps of: providing an orally disintegrable tablet of potassium chloride as described in claim 1 to a patient; placing said orally disintegrable tablet in the mouth of said patient; allowing said tablet to substantially disintegrate within said patient's mouth within about 30 seconds; and allowing said patient to swallow the resulting slurry.

23. The tablet of claim 1, wherein the tablet is between about 1,300 and about 2,800 mg and contains between about 10 and about 20 milliequivalents of potassium.

24. The tablet of claim 1, wherein the tablet dissolves or disintegrates in the mouth in 45 seconds or less.

* * * * *

UNITED STATES PATENT AND TRADEMARK OFFICE
CERTIFICATE OF CORRECTION

PATENT NO.    : 6,365,182 B1
DATED         : April 2, 2002
INVENTOR(S)   : Rajendra K. Khankari, John Hontz and Sara J. Chastain It is certified that error appears in the above-identified patent and that said Letters Patent is hereby corrected as shown below:

Column 9,
Line 52, delete "millieguivalents" and insert -- milliquivalents --;

Column 10,
Line 59, after "to" insert -- be complementary to this particle size of said coated potassium chloride";

Signed and Sealed this

Eighth Day of October, 2002

Attest:

Attesting Officer

JAMES E. ROGAN
Director of the United States Patent and Trademark Office